(12) United States Patent
Bauernschmid

(10) Patent No.: US 6,318,165 B1
(45) Date of Patent: Nov. 20, 2001

(54) DEVICE FOR MEASURING THE STICKINESS OF A FLOWABLE MEDIUM

(76) Inventor: Peter Bauernschmid, Stoetten 14, D-83317 Teisendorf (DE)

( * ) Notice: Subject to any disclaimer, the term of this patent is extended or adjusted under 35 U.S.C. 154(b) by 0 days.

(21) Appl. No.: 09/674,350
(22) PCT Filed: Apr. 27, 1999
(86) PCT No.: PCT/EP99/02850
§ 371 Date: Dec. 21, 2000
§ 102(e) Date: Dec. 21, 2000
(87) PCT Pub. No.: WO99/57540
PCT Pub. Date: Nov. 11, 1999

(30) Foreign Application Priority Data

Apr. 30, 1998 (DE) .............................................. 198 19 455

(51) Int. Cl.[7] .......................... G01B 21/08; G01N 13/00; B41F 31/00
(52) U.S. Cl. .................... 73/150 R; 73/150 A; 73/64.49; 101/349.1
(58) Field of Search ............................. 73/64.49, 150 R, 73/150 A; 106/31.15; 524/271; 101/349.1

(56) References Cited

U.S. PATENT DOCUMENTS 4,294,111 * 10/1981 Rutledge et al. .................. 73/150 R

FOREIGN PATENT DOCUMENTS

19516192 * 9/1996 (DE) .............................. G01N/33/32

* cited by examiner

Primary Examiner—Daniel S. Larkin
Assistant Examiner—Jay L. Politzer
(74) Attorney, Agent, or Firm—Reed Smith LLP

(57) ABSTRACT

A device is disclosed for measuring the stickiness of a flowable medium, in particular a printing ink, which is led as a layer between two surfaces that can be moved in the same direction, through a convergence zone, a pressure zone and a divergence zone; it being possible to use a measuring device to measure, as a measure of the stickiness, that force which is needed to separate the surfaces from each other. At least one surface is led on a circularly cylindrical path. The two surfaces are driven positively in the same direction and at the same speed. The surfaces contain, at least in some sections, those materials of which the surfaces which are assigned to each other during the processing of the medium to be tested in intended devices, such as printing machines, are composed. At least one of the two surfaces used to transfer the measured value is arranged on a supporting body directly or via a measured-value transmitter, having at least one area of set extensibility and is connected to measuring devices for establishing the magnitude and the direction of that force with which the surface is lifted off the supporting body, extending the extensible area, during the separation or splitting of the layer adhering to the surface. The measuring devices can be moved synchronously together with the moving surface.

13 Claims, 4 Drawing Sheets

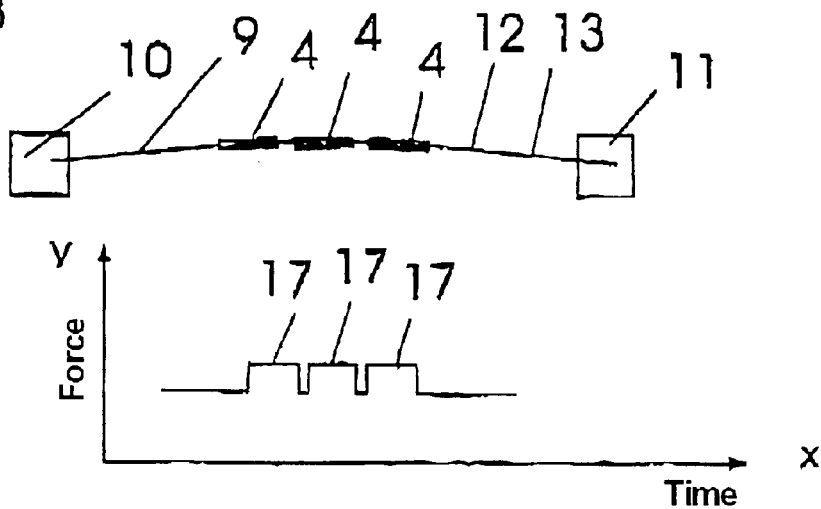
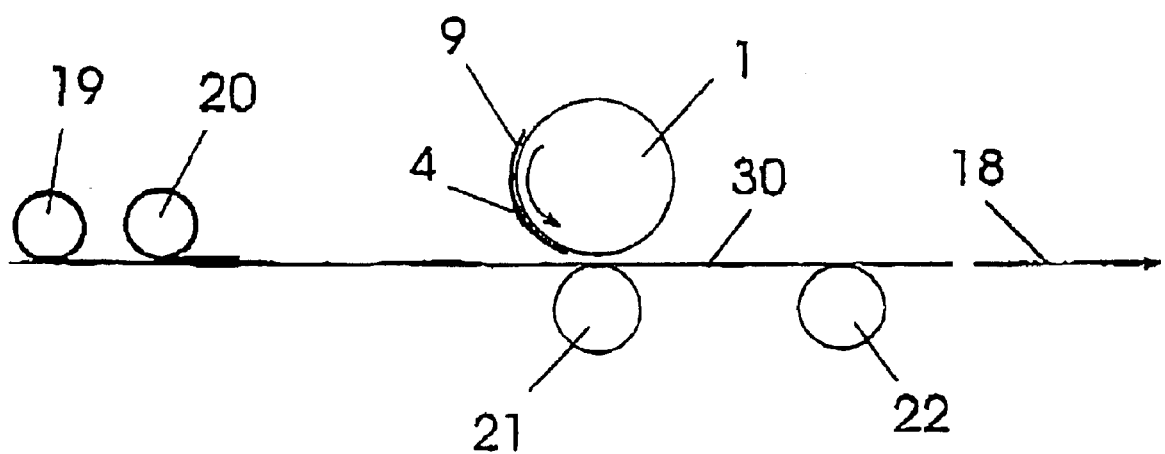

DEVICE FOR MEASURING THE STICKINESS OF A FLOWABLE MEDIUM

BACKGROUND OF THE INVENTION a) Field of the Invention

The invention relates to a device for measuring the stickiness of a flowable medium, in particular a printing ink, which is led as a layer between two surfaces that can be moved in the same direction, through a convergence zone, a pressure zone and a divergence zone, it being possible to use a measuring device to measure, as a measure of the stickiness, that force which is needed to separate the surfaces from each other.

In this case, the term stickiness is interned to include, in particular, the tack-and other rheological properties, such as viscosity.

b) Description of Related Art

In a device of this type disclosed by DE-A-19 00 328, the flowable medium to be tested is brought, in an accurately metered quantity, between two rotatable bodies, of which one is driven and the other is carried along by a frictional connection. In this case, a lever arrangement is used to measure the force which is necessary to separate the two bodies from each other. This device has the fundamental disadvantage that, as a result of driving only one rotatable body and carrying the second rotatable body along via the flowable medium to be measured, shear forces occur in this medium, which lead to a change in the rheological properties of the medium to be tested, which results in the set force for determining the tack which, during its measurement, is intended to be perpendicular to the two surfaces between which the medium to be measured is located, is falsified. A further disadvantage of this and other known devices is basically that, during the testing of printing inks and their lithographic properties, no account can be taken of those influences which result, for example, during the application of the flowable medium, for example a printing ink, to paper or other materials, since the device comprises two rotating bodies with metal and/or rubber surfaces but that, for example, the preconditions prevailing in a printing machine cannot be simulated with such a device. Furthermore, it is not possible either to determine the influence of the layer thickness of the applied medium as a function of the material of the surfaces on the tack value. Nor is there any possibility of establishing the superimposition, taking place during multicolor printing, of various flowable media, with regard to their influence on the tack. All such testing possibilities are impossible with this known device and also further devices which have been disclosed.

OBJECT AND SUMMARY OF THE INVENTION

The primary object of the invention is to configure a device of the type explained at the beginning in such a way that the stickiness values and, in particular, tack values and their changes which occur during the application, transfer, multiple covering, when being changed by the addition of further substances and during the preparation of flowable media, in various areas, for example in distributor mechanisms, on the impression cylinder or on the printing material of printing machines, can be measured in accordance with the relationships which actually occur.

In a device of the-type specified further above, according to the invention, this object is achieved in that at least one surface is led on a circularly cylindrical path, in that both surfaces can be driven positively in the same direction and at the same speed, in that both surfaces contain, at least in some sections, those materials of which the surfaces which are assigned to each other during the processing of the medium to be tested in intended devices, for example printing machines, are composed, in that at least one of the two surfaces used to transfer the measured value is arranged on a supporting body, directly or via a measured-value transmitter, has at least one area of set extensibility and is connected to measuring devices for establishing the magnitude and the direction of that force with which the surface is lifted off the supporting body, extending the extensible area, during the separation or splitting of the layer adhering to the surface, and in that the measuring devices can be moved synchronously together with the moving surface.

An important refinement of the device according to the invention is that the two surfaces can be driven in the same direction at the same speed, so that the flowable medium located between these surfaces and to be tested is not subjected to any significant shear forces which could lead to a change in the rheological properties of this flowable medium. In order to achieve these identical speeds, it is necessary for one of the surfaces to be led on a circularly cylindrical path, that is to say for this surface to be part of a circular cylinder. Although the second surface can be flat, it must also be able to be moved at the same speed, which corresponds to the circumferential speed of the circular cylinder. Of course, for the continuous measurement of the tack values, it is advantageous if both surfaces are led on circularly cylindrical paths, since in this way the interruption in time, needed to return the flat surface into the starting position without contact, is dispensed with.

A further decisive feature of the present invention is to be seen in the fact that the surfaces which are in contact with the flowable medium during the measuring operation correspond, with regard to the material selection, to those surfaces which are used in the devices in which the flowable medium to be measured is employed in the intended use. For example, one surface consists of the paper to be printed or another material to be printed, and the other surface consists of the material of which the press roll or other printing device also used in a printing machine consists. In this way, the conditions which are simulated are exactly those which are also present in the device in the intended application, that is to say in a printing machine. For those skilled in the art, it is necessary to know how a printing ink behaves during printing, where specific contents of these printing inks, for example oils, water, are picked up by the material to be printed, that is to say the paper, for example, as a result of which the rheological property of this printing ink is changed. In the previously usual measuring device, in which the materials present from the intended devices are not used, it is not possible either for these corresponding properties and changes in the flowable medium to be established. Thus, for example in the case of a measuring device which comprises a steel roll and a rubber roll, the effect will never occur such as occurs when a paper surface is used, to which the flowable medium to be tested adheres during the measuring operation.

Finally, it is also particularly significant that the measuring devices which are used to establish the magnitude and the direction of the forces occurring are moved together with the surfaces at which the forces occur. By this means, via the measuring transmitter on to [sic] the respectively associated measuring devices, the forces which, result from the medium to be tested adhering to the surface, and the forces resulting during the separation of the medium from this surface are registered at any point of the adhering area, so that the complete sequence of a separation or splitting operation can be registered with regard to the magnitude of the force and the direction of the force. Since the measuring devices are moved as well, they are able to transfer the sensed values continuously to evaluation devices, without any changes occurring in the medium to be tested as the result of any quiescent pauses, which are necessarily unavoidable in some known measuring devices. As a result of this configuration according to the invention, the measuring devices are, so to speak, always at the point of occurrence and are thus able to sense the entire range of the changes in the rheological properties during the splitting. Of course, during this measuring operation, it is necessary for the surface considered, to which the medium to be tested adheres, to be connected to at least one extensible area, it being of no consequence whether this surface is itself extensible or the extensibility is formed in the measuring transmitter at any point on the latter, that is to say either in the end area or in the areas located between.

When, at the beginning, the measurement of the stickiness of a flowable medium is mentioned, this is to be understood as meaning all types of rheological properties. When registering the tack of a flowable medium, it is only the force occurring perpendicular to the surface during the separation or splitting operation of the medium which is measured. If, however, the forces which run at an angle and are established towards the end of the splitting operation are recorded, it is then possible here to assess other properties, for example the viscosity of the medium. The term "stickiness [lacuna] is therefore intended to express a certain generic term, which of course also includes the tack as a preferred special case.

In order to be able to adjust the device to the various materials to be tested, it is advantageous if, in further refinement of the invention, the distance between the surfaces and the speed of movement of these surfaces can be adjusted. In this way, controlled shear forces can also be produced, in order to create relationships close to those occurring in practice. Although the arrangement of the measuring device is independent of the shape of the supporting body, it is advantageous for continuous measurement if the surface serving as a measuring transmitter is fitted to a cylindrical supporting body and the measuring devices are arranged in the interior of the supporting body. A cylindrical supporting body with just such a cylindrical surface is significantly more suitable to pick up successive measurement data, and in particular for the continuous testing of the medium, than a surface which is moved linearly, which has to be brought back again and again to its initial location.

If, in further refinement of the invention, a number of movable surfaces are assigned to the surface which senses the forces and transmits them to measuring devices, in this way either the processes during multicolor printing can be simulated, in which a number of flowable media with different rheological properties are layered one above another, or the processes of splitting back can be tested in one and the same medium, that is to say those processes can be tested which occur during the multiple, successive splitting of the material to be tested in a divergent area between two moving surfaces. Using this arrangement, it is also possible to test the effects of the application of additives, for example of water, to the flowable medium. This application is possible by using one of these multiple additional moving surfaces.

In this case, it is particularly advantageous if the further associated surfaces are circularly cylindrical, since the actions on the layer to be measured of the flowable medium can, be exerted much better by means of rotating surfaces than with flat moving surfaces.

A basic configuration of the arrangement for registering the forces according to the invention consists in the measuring devices for measuring the magnitude and direction of the force between the surfaces being connected mechanically to the surface or to the measuring transmitter. Here, therefore, a mechanical connection is used between the surface or the measuring transmitter and the measauring device and transmits these forces, acting on the surface, to the measuring device.

If a number of mechanical connections to the surface or to the measuring transmitter, at a distance from one another as viewed in the direction of movement, are formed, then successive steps in the development of the buildup of force during the splitting operation can be displayed.

It is also possible to provide an optical measuring device inside a supporting body to detect the physical deflection of the measuring transmitter. Here, optical measuring devices are able to establish the changing distances of the measuring transmitter with respect to the supporting body, for example through appropriate holes in the wall of the supporting body.

If, in further refinement of the invention, two circularly cylindrical supporting bodies with deflectable surfaces and a measured-value transmitter are provided and, together with the measuring devices, form a measuring mechanism, the said surfaces holding the medium to be tested between them, then relatively long, virtually parallel distances between mutually opposite measured-value transmitters can be formed, in which the flowable medium to be tested is located. This makes it possible, in particular in connection with a further refinement of the invention, in which the deflectable surface consists of a material that does not influence the medium, to measure the rheological property, in particular the tack, which is intrinsic to the medium to be measured, uninfluenced by external influences, since the splitting operation can be measured at both surfaces to which the medium adheres over a relatively long distance with regard to the development of the force. In this way, the so-called "original tack" which is inherent in the material and not influenced by any external influences can be established.

If it is desired to establish the rheological properties of a flowable medium not only within a gap between two moving surfaces but also under the action of shear forces, such as occurs when rolls reciprocate in an inking unit or distributor unit, then it is advisable to configure the device in such a way that, between the two measuring mechanisms formed from the supporting body and measured-value transmitters [sic], there is arranged a roll which interacts with both measuring mechanisms and, in addition, can be driven displaceably to and from in its axial direction. In this case, the splitting forces occurring in the divergent area also have superimposed on them the shear forces brought about by the reciprocating movement, which enter into the measurement result and permit the magnitude and direction of the forces in such inking or distributor units to be registered in a manner which is close to reality.

The device according to the invention may also be used for testing the various materials of the surfaces used, for which purpose a flowable testing medium whose properties are known is employed.

The invention will be explained in more detail below using a number of exemplary embodiments illustrated in the drawing.

BRIEF DESCRIPTION OF THE DRAWINGS

FIG. 3: shows a deflectable measured-value transmitter, which forms part of the device according to the invention, in conjunction with a force diagram which can be established on this measured-value transmitter;

FIG. 4: shows another exemplary embodiment of a device according to the Invention in conjunction with a multiple application of the medium to be tested;

DESCRIPTION OF THE PREFERRED EMBODIMENTS

Figure 1:
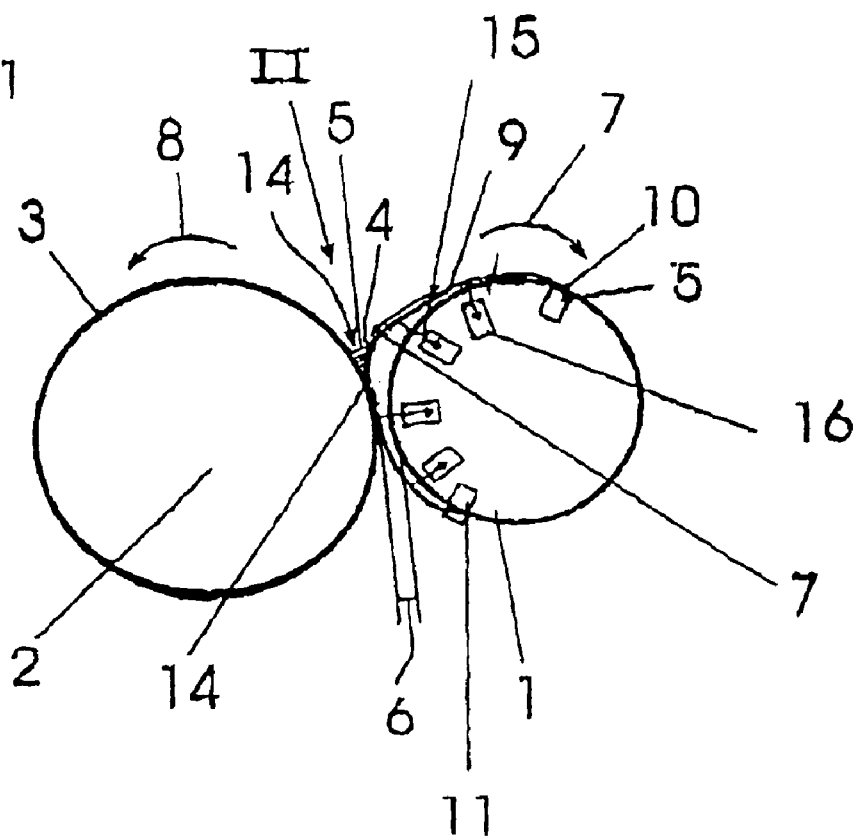
FIG. 1: shows a schematic sectional illustration through a device according to the invention.
Figure 2:
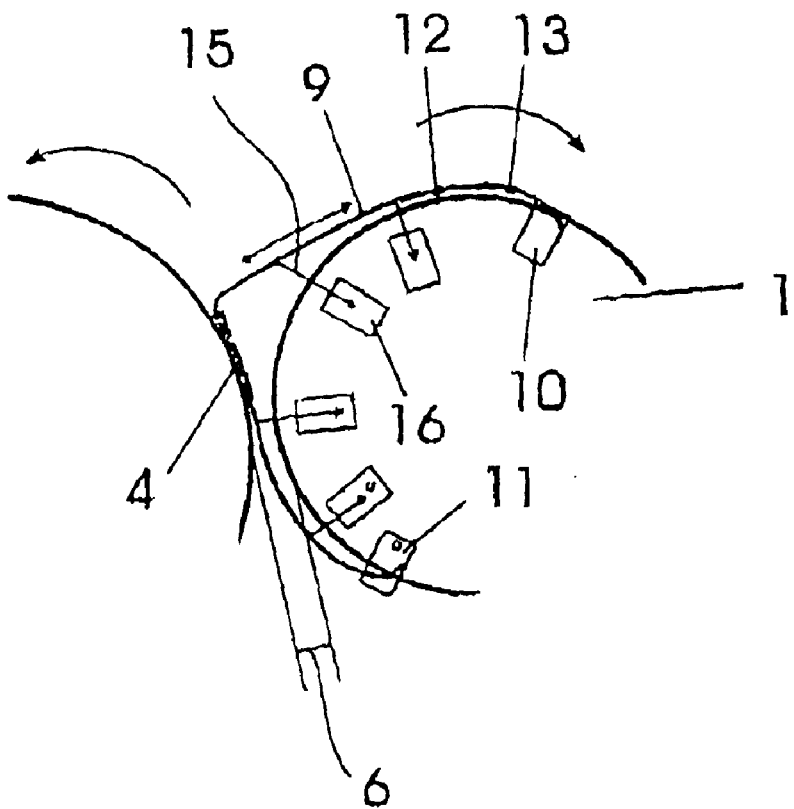
FIG. 2: shows an enlarged illustration of the area designated by II in FIG. 1.

FIGS. 1 and 2 reveal the basic principle of the invention. This device has two cylindrical supporting bodies in the form of rolls 1 and 2, which are provided with surfaces 3 and 4 between which the flowable medium 5 to be tested can be tested with regard to the stickiness and other rheological properties and, in particular, with regard to the tack of this medium. Surfaces means those areas with which the flowable medium can come into contact when it is squeezed through between the two supporting bodies 1 and 2 in an adjustable gap 6. The two supporting bodies 1 and 2 are rotated in the direction of the arrows 7 and 8, specifically in such a manner that the surfaces 3 and 4 are moved at the same speed, so that no shear forces are exerted on the medium 5 to be tested. The surface 3 is arranged directly and firmly on the supporting body 2, the material forming this surface 3 consisting of rubber, for example, and simulating an applicator roll in a printing unit. The rotating supporting body 1 is fitted with a measured-value transmitter 9 which initially rest closely against it and is clamped in at its ends in holders 10 and 11, which can also be designed as measuring devices. This measured-value transmitter, which rests closely against the supporting body 1 when there is no flowable medium 5, has at least one extensible area, for example between the points 12 and 13, in order to permit a deflection or a lifting of this measured-value transmitter 9 from the supporting body 1. Formed in this measured-value transmitter 9 are areas which form parts of a surface 4 which is intended to be brought into contact with the medium 5 to be tested, in order to measure the forces occurring in the diverging gap area 14 during the splitting of the flowable medium. This surface 4, formed from the individual sections, consists of the material which comes into contact during the intended application of the flowable medium. For example, in printing, this is the case in which the ink is applied to paper. The parts of the area 4 therefore represent paper, for example. In conjunction with the surface 3, consisting of rubber, for example, here the relationships during the printing of paper are simulated in a manner close to practice, so that the splitting forces which occur during such a printing operation can actually be measured. When the supporting body 1 and 2 [sic] is rotated in the direction of the arrows 7 and 8, the flowable medium 5 is torn apart in the divergent splitting area 14, which produces a force which, acting on the surfaces 4, lifts the measured-value transmitter 9 off the supporting body 1. As can be seen in particular from the somewhat larger illustration in FIG. 2, the measured-value transmitter 9 is connected via mechanical connecting parts, for example threads 15, to measuring devices 16, which are arranged in the interior of the supporting body 1 and moved together with the latter and therefore also with the surface 4 involved in the measuring operation. From the different deflection of the mechanical connections 15, and also from the respective direction, the magnitude and direction of the force occurring during the splitting operation or during the separation operation can be determined. These illustrations in FIGS. 1 and 2 reveal that two surfaces, which are in contact with the medium, are moved, to be specific at the same speed, at least one surface being moved on a circular path. One of these surfaces is itself extensible or arranged on an extensible measured-value transmitter 9, this deflectable surface or its associated measured-value transmitter being connected to measuring devices 16, in order to establish the forces occurring during the splitting operation.

The following examples show various application areas, it being possible in each case to see the primary principle in the fact that the surfaces to be brought into connection with the medium consist of those materials such as are also employed in practice when applying the medium to be tested. In the case of printing machines, these are rubber rolls, appropriately prepared metal plates, relief plates, papers to be printed or other materials to be printed.

FIG. 3 shows a measured-value transmitter 9, which is clamped in at the ends into holders 10 and 11, and surfaces 4 that are connected directly to the measured-value transmitter. These surfaces are either made of a material which is not extensible or is quite generally not suitable for the transmission of measured values. Provided for this purpose is the measured-value transmitter 9, which has an extensible area between the points 12 and 13. Of course, the measured-value transmitter 9 can also be extensible overall. However, it is also possible for the holding device 10 and 11 to be connected via a spring to an unextensible measured-value transmitter. The form in which the extensible area is formed, and whether a number of extensible areas are provided, is of secondary importance, since the significant fact is that the area or the measured value transmitter connected to it can be lifted off the supporting body when the latter moves. This lifting movement is then transmitted to the corresponding measuring devices, as already explained. Also to be seen in FIG. 3 is a force diagram, plotted over time, the respective signals 17 being produced during the deflection of an area of the surface 4. From these signals 17, it is possible to register and read off both the magnitude of the force and the duration of the same.

FIG. 4 shows a device in which a measured-value transmitter 9 with a surface 4 is arranged on a rotatable supporting body 1. This time, a flat surface 30, which can be moved in the direction of the arrow 18, and not a rotating surface, interacts with the said surface 4. On this surface 30, which has the same speed as the surface 4, in each case identical or different media to be tested are applied by means of two applicator rolls 19 and 20 connected one after another, in order to test the behavior in the case of two layers placed one above another and consisting of identical or different media. The movable surface 30 is supported by a supporting roller 21. A further supporting roller 22 is provided for the case where an elastic pressure opposing the circulating supporting body 1 is desired, and the latter is arranged between the two supporting rollers 21 and 22. The measured values are registered by the measuring mechanism, formed by the supporting body 1, measured-value transmitter 9 and surface 4, in the same way as described in connection with FIGS. 1 and 2.

Figure 5:
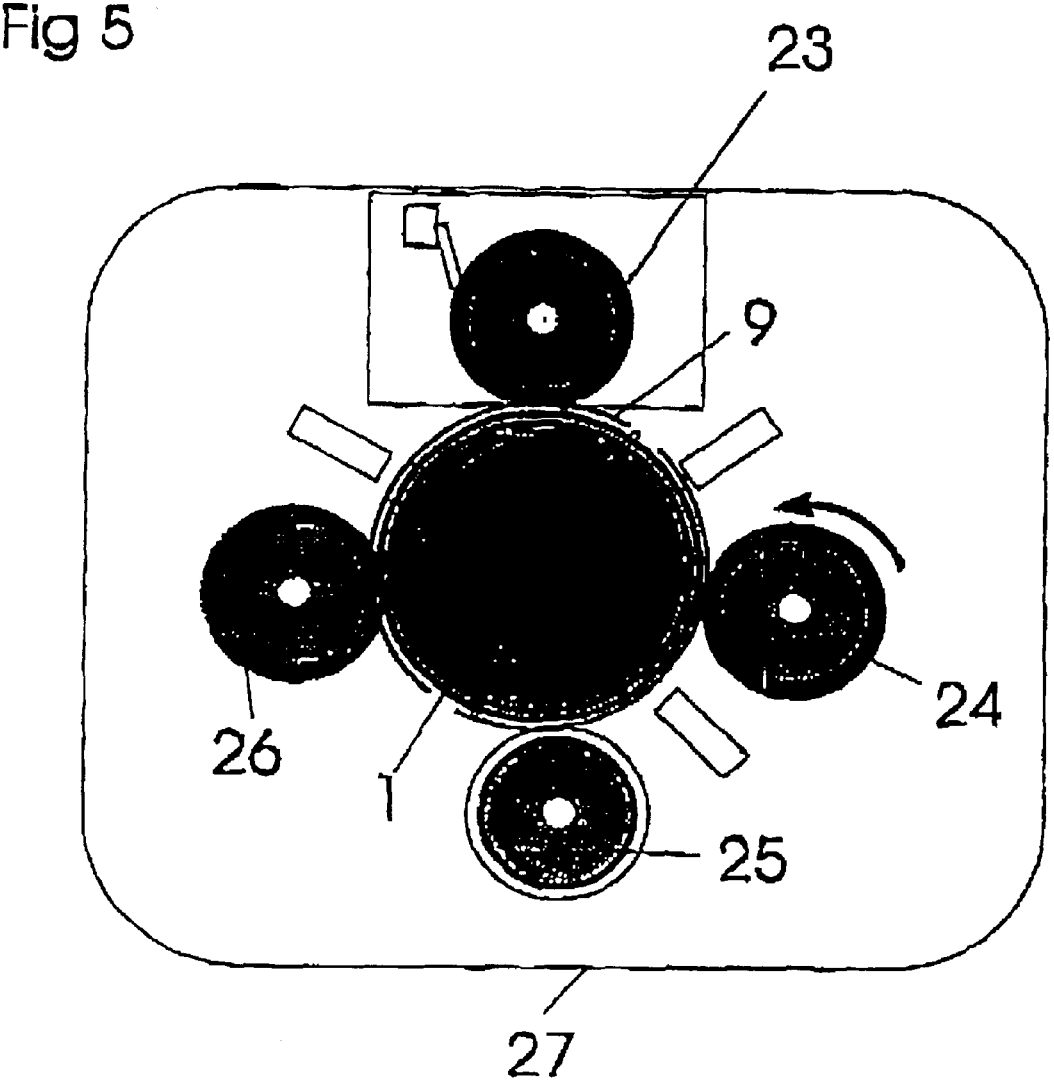
FIG. 5: shows a device according to the invention having a number of additional surfaces for testing the processes during multicolor printing or the frequent repetition of splitting back.

The device illustrated in FIG. 5 comprises a measuring mechanism built up from a supporting body 1, measured-value transmitter 9 and the measuring devices arranged in the interior of the supporting body 1, and also a number of further circularly cylindrical surfaces in the form of driven rolls 23 to 26 which are distributed uniformly on the circumference of this measuring mechanism and which, depending on the application, are given different tasks. In the first application, the flowable medium to be tested can be applied by the roll 23, and the remaining rolls 24 to 26 with their circularly cylindrical surfaces are used to produce successive splitting-back operations, that is to say the medium applied and split by the roll 24 and its associated circularly cylindrical surfaces is split again by the following rolls 25 and 26. As a result of these multiple splitting actions, the rheological property of the flowable medium to be tested is changed. With the aid of the measuring mechanism arranged at the center, it is possible to establish and to evaluate the different effects of this multiple repeated splitting-back. The entire arrangement is accommodated in a housing designated by 27, which can be conditioned in terms of temperature and humidity and can also serve as a protective means for preventing the media to be tested being able to evaporate into the environment.

Figure 6:
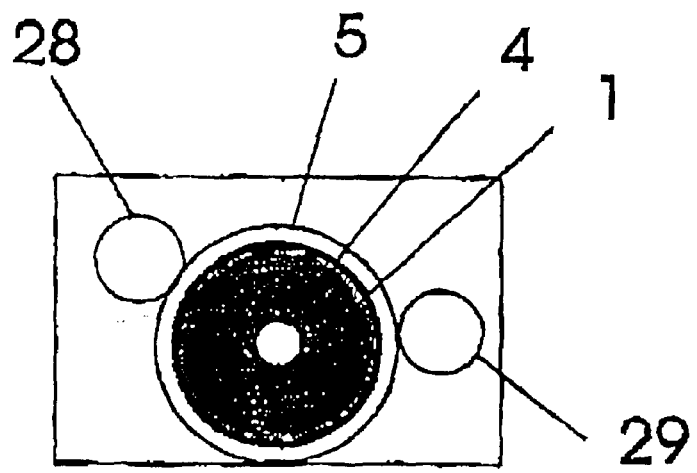
FIG. 6: shows a device of the invention for measuring the influence of the medium during multiple splitting and as a result of the introduction of additives into the flowable medium.

FIG. 6 shows a central measuring mechanism with a supporting body 1, a surface 4 as also illustrated in FIG. 1, this measuring mechanism being assigned two circularly cylindrical surfaces 28 and 29, via which a further substance is added to the medium 5, in order to test the changes in the rheological properties when the medium 5 originally applied is changed by the addition of further substances. In practice, such an arrangement is requested and significant when the influence of the addition of water to a printing ink is to be tested, as is the case, for example, in offset printing, where water is used as a release agent and, because of its presence, of course exerts an influence on the stickiness and also an influence on the tack of the printing ink.

Figure 7:
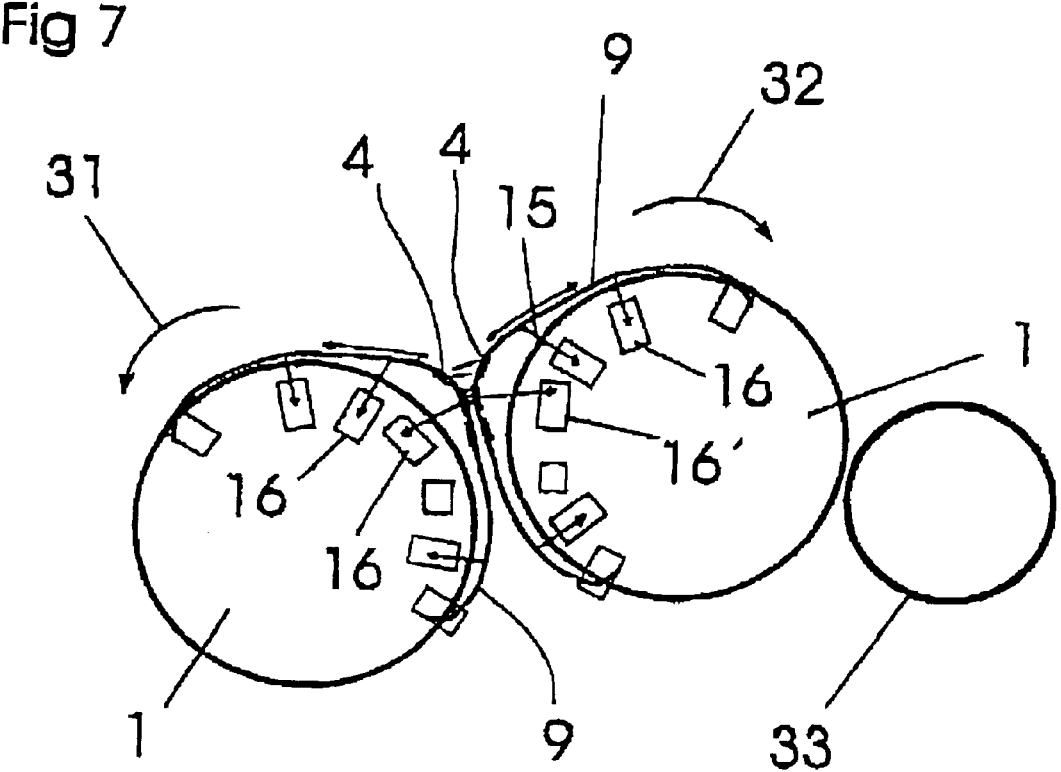
FIG. 7: shows a double arrangement of a device according to FIG. 1.

FIG. 7 shows the association of two identical measuring mechanisms, each measuring mechanism having a supporting body 1, a measured-value transmitter 9, surfaces 4 integrated thereon and measuring devices 16 arranged in the interior of the supporting body 1. A flowable medium introduced between the measured-value sensor 9 and its associated surfaces 4 leads to the measured-value transmitters 9 being lifted during the rotation of the measuring mechanisms in the direction of the arrows 31 and 32, and therefore to a display on the respective measuring devices 16. This arrangement is particularly advantageous when, by using surfaces 4 which have no influence on the flowable medium, the stickiness inherent in this flowable medium and, in particular, the original inherent tack is also to be established. In this case, the tack is derived from the value of the force which occurs perpendicular to the cooperating surface, which is the case, for example, in the measuring devices designated by 16. The other measuring devices are used to determine further rheological properties, for example the viscosity of the flowable medium to be tested. A further roll 33 is provided in order, for example, to register the effects of a material already split between the surface 4 when it is applied to the roll, which may, for example, have a paper surface. The roll can also carry the flowable medium.

Figure 8:
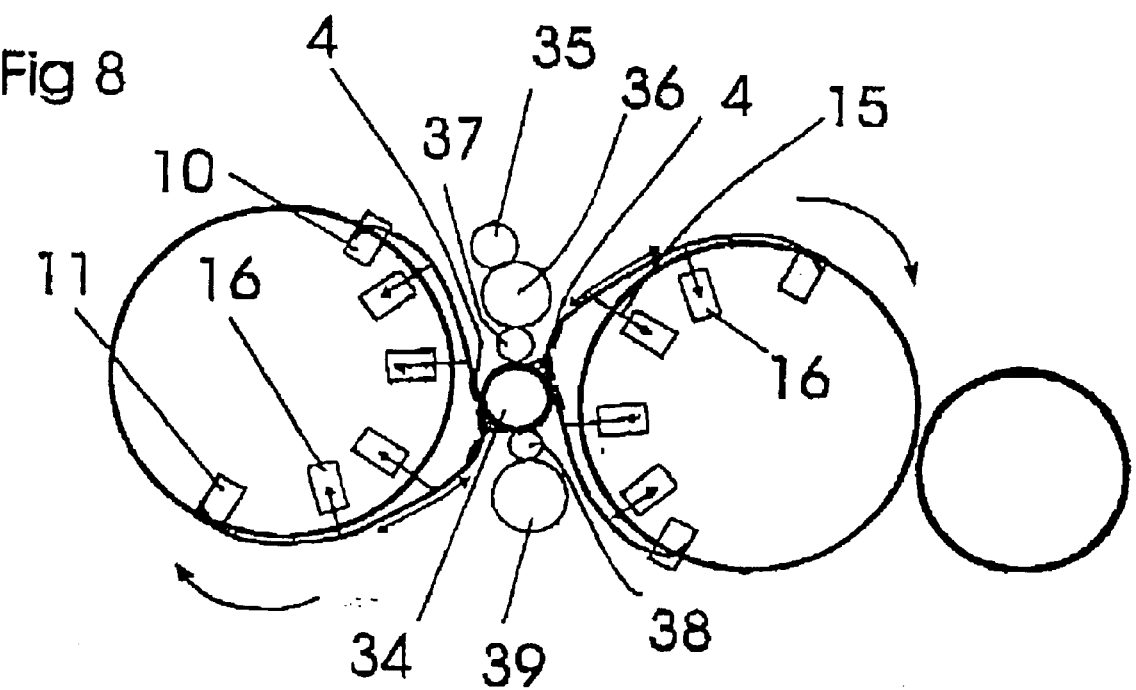
FIG. 8: shows a modification of the arrangement according to FIG. 7.

In the arrangement according to FIG. 8, two measuring mechanisms corresponding to FIG. 7 are provided, are at a greater distance and accommodate between them a roll body 34, which is connected to the respective surfaces 4 of the two measuring mechanisms via a flowable medium which is introduced. The latter is applied to the roll 34 via a number of rolls 35, 36 and 37, to be specific in such an excess that it flows away via further rolls 38 and 39, or in just such a quantity, as is picked up by the roll 39. The roll 34 that is connected to the two measuring mechanisms is provided in order to determine, in such an ink flow in a roller inking mechanism, the influence on the respective rheological properties as the ink flows through such a roller mechanism. In this case, which also takes place in practice in a printing unit during the distribution of the inks, the roll 34 can execute reciprocating movements, that is to say movements in the direction of its longitudinal axis, which produces shear forces on the flowable medium between the roll 34 and the surfaces 4 of the measuring mechanisms.

Of course, these shear forces change the rheological properties of the medium, the two measuring mechanisms being capable of registering these properties, changed in this way, by measurement and of forwarding them to computer-aided evaluation devices.

While the foregoing description and drawings represent the present invention, it will be obvious to those skilled in the art that various changes may be made therein without departing from the true spirit and scope of the present invention.

What is claimed is:

1. A device for measuring the stickiness of a flowable medium, in particular a printing ink, which is led as a layer between two surfaces that can be moved in the same direction, through a convergence zone, a pressure zone and a divergence zone, it being possible to use a measuring device to measure, as a measure of the stickiness, that force which is needed to separate the surfaces from each other, comprising;

at least one surface being led on a circularly cylindrical path;
   said two surfaces being driven positively in the same direction and at the same speed;
   said surfaces containing, at least in some sections, those materials of which the surfaces which are assigned to each other during processing of a medium to be tested in intended devices, such as printing machines, are composed;
   at least one of the two surfaces used to transfer the measured value being arranged on a supporting body, directly or via a measured-value transmitter, having at least one area of set extensibility and being connected to measuring devices for establishing the magnitude and the direction of that force with which the surface is lifted off the supporting body, extending the extensible area, during the separation or splitting of the layer adhering to the surface; and said measuring devices being able to be moved synchronously together with the moving surface.

2. The device as claimed in claim 1, wherein both surfaces are led on a circularly cylindrical path.

3. The device as claimed in claim 1, wherein the distance between the surfaces can be adjusted.

4. The device as claimed in claim 1, wherein the speed of movement of the surfaces can be adjusted.

5. The device as claimed in claim 1, wherein the surface serving as a measured-value transmitter is fitted to a cylindrical supporting body, and wherein the measuring devices are arranged in the interior of the supporting body.

6. The device as claimed in claim 5, wherein a number of movable surfaces are assigned to the surface which senses the forces and transmits them to measuring devices.

7. The device as claimed in claim 5, wherein the further associated surfaces are circularly cylindrical.

8. The device as claimed in claim 1, wherein the measuring devices for measuring the magnitude and direction of the force between the surfaces are connected mechanically to the surface or to the measuring transmitter.

9. The device as claimed in claim 8, wherein a number of mechanical connections to the surface or to the measuring transmitter, at a distance from one another as viewed in the direction of movement, are formed by a number of measuring devices.

10. The device as claimed in claim 1, wherein an optical measuring device is provided inside a supporting body to detect the physical deflection of the measuring transmitter.

11. The device as claimed in claim 1, wherein two circularly cylindrical supporting bodies with deflectable surfaces and a measured-value transmitter are provided and, together with the measured-value devices, form a measuring mechanism, the said surfaces holding the medium to be tested between them.

12. The device as claimed in claim 11, wherein the deflectable surface consists of a material that does not influence the medium.

13. The device as claimed in claim 11, wherein between the two measuring mechanisms formed from the supporting body and measured-value transmitter, there is arranged a roll which interacts with both measuring mechanisms and, in addition, can be driven displaceably to and fro in its axial direction.

* * * * *